United States Patent [19]

Mueller et al.

[11] Patent Number: 4,918,218

[45] Date of Patent: Apr. 17, 1990

[54] PREPARATION OF ACETIC ACID AND METHYL ACETATE

[75] Inventors: Franz-Josef Mueller, Wachenheim, Fed. Rep. of Germany; Dominique Matt, Strasbourg, France

[73] Assignee: BASF Aktiengesellschaft, Ludwigshafen, Fed. Rep. of Germany

[21] Appl. No.: 623,973

[22] Filed: Jun. 25, 1984

[30] Foreign Application Priority Data

Jul. 1, 1983 [DE] Fed. Rep. of Germany ....... 3323654

[51] Int. Cl.$^4$ .................... C07C 51/12; C07C 53/08; C07C 67/36; C07C 69/14
[52] U.S. Cl. .................... 560/232; 502/184; 502/185; 502/245; 502/259; 502/326; 562/519
[58] Field of Search .................... 560/232; 562/519; 502/184, 185, 245, 259, 326

[56] References Cited

U.S. PATENT DOCUMENTS

| | | | |
|---|---|---|---|
| 2,650,245 | 8/1953 | Thomas et al. | 562/519 |
| 2,650,246 | 8/1953 | Thomas et al. | 562/519 |
| 3,856,856 | 12/1974 | Nozaki | 562/519 |

FOREIGN PATENT DOCUMENTS

| | | | |
|---|---|---|---|
| 47-3332 | 1/1972 | Japan | 562/519 |
| 731549 | of 1955 | United Kingdom . | |

*Primary Examiner*—Vivian Garner
*Attorney, Agent, or Firm*—John H. Shurtleff

[57] ABSTRACT

Preparation of acetic acid and methyl acetate by gas-phase carbonylation of methanol in the presence of a nickel-containing catalyst and in the presence of chlorine, bromine or iodine or a volatile compound of one of these halogens as a promoter, wherein the active material of the catalyst used consists of not less than 40% by weight of nickel and the catalyst contains 0.001–1 part by weight of palladium per part by weight of nickel, as well as supported catalysts whose active material contains Ni and Pd in the above ratio.

10 Claims, No Drawings

PREPARATION OF ACETIC ACID AND METHYL ACETATE

The present invention relates to an improved process for the preparation of acetic acid and methyl acetate by carbonylation of methanol in the gas phase in the presence of a nickel-containing catalyst and in the presence of chlorine, bromine or iodine or a volatile compound of one of these halogens as a promoter:

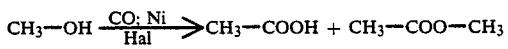

$$CH_3-OH \xrightarrow[Hal]{CO;\ Ni} CH_3-COOH + CH_3-COO-CH_3$$

The present invention furthermore relates to novel catalysts which are useful for the preparation of acetic acid and methyl acetate by gas-phase carbonylation.

It is well known that acetic acid and methyl acetate can be prepared by carbonylation of methanol in the presence of carbonyl-forming metals and of halogens or halogen compounds.

The large-scale industrial processes are liquid-phase processes employing cobalt or rhodium as the carbonyl-forming metal. However, neither process is quite satisfactory: the use of cobalt requires high pressure (about 250–700 bar) and is energy-consumptive, and rhodium, although it permits the use of lower pressure (about 35–70 bar), is extremely expensive.

According to the process described in DE-A No. 1 005 949, the carbonylation of the methanol is carried out in the gas phase under relatively low pressure, over an active carbon catalyst impregnated with nickel iodide. However, a problem in this process is that the nickel tetracarbonyl formed under the reaction conditions is desorbed by the carrier. This results in a gradual decrease in the activity of the catalyst, and the nickel tetracarbonyl which passes into the emerging product also gives rise to difficulties in the working up procedure. The DE-A (loc cit.) remedies these disadvantages in principle by re-adsorbing the desorbed nickel tetracarbonyl onto a catalyst-free carbon carrier located downstream in the reaction space, and reversing the direction of flow of the starting materials when the nickel content of the first catalyst has decreased substantially and that of the second catalyst has increased correspondingly. When the nickel concentrations in the two catalysts have once again reversed, the direction of flow of the reactants also has to be changed, these steps being repeated continually. This procedure is obviously involved and therefore uneconomical from the point of view of process engineering.

It is an object of the present invention to provide a more efficient process for the gas-phase carbonylation of methanol in the presence of a nickel catalyst.

We have found that this object is achieved by an improved process for the preparation of acetic acid and methyl acetate by gas-phase carbonylation of methanol in the presence of a nickel-containing catalyst and in the presence of chlorine, bromine or iodine or a volatile compound of one of these halogens as a promoter, wherein the active material of the catalyst used consists of not less than 40% by weight of nickel, and the catalyst contains 0.001–1 part by weight of palladium per part by weight of nickel.

We have furthermore found that it is particularly advantageous if the novel catalysts are used in the form of supported catalysts.

The invention is based on the observation that the undesirable formation of volatile nickel tetracarbonyl is substantially suppressed by the presence of the palladium, and that the catalysts therefore have a virtually unlimited life. Presumably the compounds formed under the reaction conditions are partial Ni and Pd carbonyl complexes which remain bonded to the metallic phase, or are cluster complexes which contain several central atoms and have a high molecular weight, which means that they are non-volatile.

The essential components of the active catalytic material are therefore nickel and palladium. On the other hand, the presence of other metals which are reducible under the reaction conditions, even those which do not form carbonyls, does not present problems, at least with regard to the volatility of the carbonyls.

Examples of very suitable catalysts are those whose active material contains

40–90% by weight of Ni,
0.02–10% by weight of Pd and
from 0 to about 60% by weight of Cu.

The form which the active catalytic material assumes under the reaction conditions is not known; however, it must be assumed that alloys or alloy-like agglomerates are formed.

The catalysts can be used without a carrier, for example in alloy form or in the form of moldings of the metal salts in an appropriate composition, the salts being reduced under the reaction conditions to give the metals or their alloys, and these then being converted to the active carbonyl form at the surface.

However, it is technically more useful to employ the catalysts in the form of supported catalysts containing about 5–15% by weight of the metals (calculated as metal) as the active catalytic material.

Suitable carriers are in principle all substances which are virtually inert under the reaction conditions, i.e. materials such as $SiO_2$, $TiO_2$, MgO, $Al_2O_3$ and in particular active carbon, which are conventionally also used for other catalysts; substances having a large specific surface area and therefore a correspondingly high adsorption capacity are preferred.

The carrier particles can have any desired form (e.g. spheres, cylinders, strands or rings), but should preferably be longer than 2 mm in one or more dimensions and longer than 10 mm in only one dimension.

The supported catalysts can be prepared by a conventional method, for example by impregnating the carrier with solutions of compounds of the metals, drying the material and, if required, repeating these operations the number of times required to achieve the desired metal content.

Particularly suitable solutions of the metal compounds are aqueous, alcoholic or aqueous-alcoholic solutions of the chlorides or especially of the nitrates. These solutions can also be sprayed onto the carriers.

Under the reaction conditions, the metal compounds are then reduced to the metals; however, it is advisable to carry out the reduction separately beforehand, for example by treating the catalyst with hydrogen at 150°–450° C. under 1–100 bar for 3–24 hours. It may also be advantageous to carry out the reductive hydrogenation after each individual drying process so that material which has already been applied does not go into solution once again.

Furthermore, it is advantageous to subject the dried impregnated material to after-treatment with gaseous ammonia. This procedure probably results in the conversion of some of the nickel to Ni-NH₃ complexes which can be more readily reduced and which give a more finely divided and therefore more active nickel during the reduction.

The hydrogenation can be carried out as an upstream measure in the reactor in which the carbonylation takes place.

It is also possible to apply the components separately to the carrier, and to dope a pre-prepared nickel catalyst finally with palladium. This method permits in particular the use of the small amounts of Pd conforming to the definition. In this case, it is also advantageous to apply the palladium onto the prepared catalyst from an organic solution, for example from a solution of palladium-bis(dibenzal)acetone in toluene or tetrahydrofuran. The preparation of the catalyst can also be carried out in the reverse sequence, i.e. the palladium can be applied first, followed by the nickel and, if required, other components.

As always in the case of heterogeneous catalysts, the amount of catalyst depends substantially on its surface are and can therefore only be stated approximately. As a rule, 50–250 g of active catalytic material should be available per liter of reaction space.

In the present process, the carbonylation conditions are not critical for the invention and therefore do not in principle require any definition. On the other hand, the only suitable conditions for practical operation are those under which the reaction takes place sufficiently rapidly and the formation of methane is not markedly troublesome, and which furthermore do not entail an unnecessarily high energy consumption for the generation of the reaction pressure. These practical conditions are satisfied at from 200° to 350°C., preferably from 280° to 320°C, and under a CO partial pressure of from 0.5 to 10 bar, corresponding to a total pressure of about 30 bar.

The promoter used is chlorine, bromine or in particular iodine or a volatile compound of one of these halogens, e.g. HCl, HBr or HI or in particular an organic halogen compound. The organic radical of these compounds is in principle not critical, especially since the methyl halides are formed as the most stable compounds under the reaction conditions. From the point of view of working up the reaction mixtures, it is therefore most advantageous to use a methyl halide, especially methyl iodide, from the outset.

The amount of iodine or of the iodine compound is preferably from 0.05 to 0.2 mole per mole of methanol, while the amounts of the other, somewhat less reactive halogens or their compounds are up to about twice these values.

Methanol and methyl iodide (or another promoter conforming to the definition) are advantageously mixed in liquid form with the carbon monoxide, the mixture is then vaporized and the gas mixture is fed into the reactor. If the vaporization is carried out in the reactor itself, it is advisable to ensure that the catalyst comes as little as possible into contact with the liquid, for example by arranging the catalyst at a sufficient distance from the inlet point.

Since the carbonylation is exothermic, adequate cooling must be provided. It is therefore preferable to use a tube-bundle reactor, since this permits particularly straightforward temperature control.

The residence time of the reactants is about 0.02–10 minutes.

Working up to obtain the products can be carried out in a conventional manner, so that further description in this connection can be dispensed with.

In the novel process, the space-time yields of free or bound acetic acid are about 0.1–0.3 kg per hour per liter of catalyst. Furthermore, in the course of uninterrupted experimental operation for about two weeks, no decrease in the catalyst reactivity was observed; this was in agreement with the fact that no metal carbonyls were detected in the mixture emerging from the reactor.

EXAMPLE 1

Preparation of a Ni/Pd/active carbon supported catalyst 200 g of active carbon having a specific surface area of 600 m²/g were pretreated at 120°C. and under 10 mbar and then stirred with a solution of 5 g of palladium-bis(dibenzalacetone) and 1 liter of toluene for one hour at room temperature, after which the solid material was filtered off from the solvent and then dried at 120° C. and under 10 mbar.

This material was then impregnated with a solution of 450 g of nickel(II) chloride hexahydrate in 1 liter of water, the aqueous phase was separated off and the solid material was dried at 120° C. and under 10 mbar and treated for 10 minutes with gaseous ammonia and then with nitrogen. The resulting catalyst intermediate was treated under conditions of hydrogenation, under 1 bar and at 300° C., first with a mixture of 5 vol. % of H₂ and 95 vol. % of N₂ for 2 hours and then with pure H₂ for 8 hours. The ready-to-use supported catalyst contained 8.7% by weight of Ni and 0.03% by weight of Pd (corresponding to 0.0034 part by weight of Pd per part by weight of Ni).

EXAMPLE 2

Preparation of a Ni/Cu/Pd/active carbon supported catalyst 300 g of the active carbon described in Example 1 were impregnated with a solution of 10 g of palladium acetate, 265 g of copper(II) chloride and 259 g of nickel-(II) chloride in 1,100 ml of methanol, the excess liquid was separated off and the solid was dried at 120° C. and under 10 mbar and treated for 15 minutes with gaseous ammonia and then with argon.

Reduction with hydrogen as described in Example 1 gave a ready-to-use supported catalyst which contained 3.4% by weight of Ni, 6.9% by weight of Cu and 0.5% by weight of Pd (corresponding to 0.15 part by weight of Pd per part by weight of Ni).

EXAMPLE 3

Preparation of an intermediate of a Ni/Pd/active carbon supported catalyst 300 g of the active carbon described in Example 1 were impregnated with a solution of 10 g of palladium-bis(dibenzalacetone) in 1 liter of toluene, excess toluene was separated off and the solid material was dried. This treatment was then repeated. The resulting material was then impregnated with a solution of 450 g of nickel(II) chloride in 1 liter of water, and the solid was filtered off, and dried at 120° C. and under 10 mbar for 20 hours. This catalyst intermediate contained 6.7% by weight of Ni and 0.4% by weight of Pd.

EXAMPLE 4

Carbonylation of methanol using the catalyst described in Example 1

A reaction tube having a height of 100 cm and an internal diameter of 1.8 cm was filled with 137 g of the catalyst described in Example 1 (bulk density 540 g/liter), after which a mixture of 49.7 g/hour of CO, 16.3 g/hour of methanol and 8.4 g/hour of methyl iodide (molar ratio 30.1:8.6:1) was passed continuously into the reaction tube at 300° C. and under 1 bar.

The reacted mixture was cooled to 25° C. to give a gas phase consisting of CO, 0.8 vol % of $CH_4$, 0.83 vol % of dimethyl ether and traces of other components, and a liquid phase consisting of methanol, methyl iodide, 2.0 g of water, 5.9 g of acetic acid and 6.1 g of methyl acetate.

The methanol conversion was 65%, and the yield of free and esterified acetic acid (molar ratio 1.2:1) was 80%, based on methanol used. The space-time yield of acetic acid is therefore 13 g per liter of catalyst per hour.

The duration of the experiment was 200 hours, during which no loss of activity of the catalyst was observed, and neither Ni nor Pd was detected in the reacted mixture.

EXAMPLE 5

Carbonylation of methanol using the catalyst described in Example 2

38.4 g/hour of CO, 19.7 g/hour of methanol and 10.3 g/hour of methyl iodide (molar ratio 18.9:8.5:1) were reacted at 310° C. over 137 g of the catalyst of Example 2 (bulk density 540 g/liter), using the procedure described in Example 4.

The yield of free and esterified acetic acid (molar ratio 2.2:1) was 73%, and the space-time yield of acetic acid was 60 g per liter of catalyst per hour.

In the course of the experimental period of 120 hours, no loss in the activity of the catalyst was observed, and no metals were detected in the reacted mixture.

EXAMPLE 6

Activation of the catalyst intermediate described in Example 3, followed by carbonylation of methanol A tube reactor having a height of 1 m and an internal diameter of 6 mm was filled with 15.4 g of the catalyst intermediate described in Example 3, and a stream of $H_2$ under 25 bar was passed in for 12 hours at 280° C.

After the hydrogenation, 31.2 g/hour of CO, 13.5 g/hour of methanol and 1.76 g/hour of methyl iodide (molar ratio 90:34:1) were passed through the catalyst at 280 °C. and under 1 bar.

The yield of free and esterified acetic acid (molar ratio 0.3:1) was 41.6%, based on the methanol used, and the space-time yield was 212 g per liter of catalyst per hour.

During an experimental time of 280 hours, the catalyst completely retained its activity, and no metal passed into the reacted mixture.

We claim:

1. In a process for the preparation of acetic acid and methyl acetate by gas-phase carbonylation in the presence of a nickel-containing catalyst and in the presence of chlorine, bromine or iodine or a volatile compound of one of those halogens as a promoter, the improvement which comprises:
   carrying out the reaction with a catalyst in which the active material consists essentially of not less than 40% by weight of nickel, and 0.001–1 part by weight of palladium per part by weight of nickel.

2. A process as claimed in claim 1, wherein the catalyst is used in the form of a supported catalyst.

3. A process as claimed in claim 1, wherein the catalyst carrier is active carbon.

4. A process as claimed in claim 1, wherein the promoter used is methyl iodide.

5. Process as claimed in claim 1 wherein the active material is supported on a substantially inert carrier selected from the group consisting of $SiO_2$, $TiO_2$, MgO, $Al_2O_3$ and active carbon.

6. A process as claimed in claim 1, wherein the process is carried out with a catalyst in which the active material consists essentially of
   (a) 40–90% by weight of nickel,
   (b) 0.02–10% by weight of palladium, and
   (c) 0–60% by weight of copper.

7. A process as claimed in claim 6, wherein the active catalyst is supported on a substantially inert carrier.

8. A process as claimed in claim 7, wherein the carrier consists of active carbon.

9. A process as claimed in claim 6, wherein the active material is supported on a substantially inert carrier selected from the group consisting of $SiO_2$, $TiO_2$, MgO, $Al_2O_3$ and active carbon.

10. A process as claimed in claim 9, wherein the inert carrier supports about 5–15% by weight of the active material calculated as the metal.

* * * * *

UNITED STATES PATENT AND TRADEMARK OFFICE
CERTIFICATE OF CORRECTION

PATENT NO. : 4,918,218
DATED : April 17, 1990
INVENTOR(S) : Franz-Josef Mueller and Dominique Matt It is certified that error appears in the above-identified patent and that said Letters Patent is hereby corrected as shown below:

IN THE CLAIMS:   Column 6

Claim 1, line 2:   after "carbonylation" insert --of methanol--.

Claim 1, line 5:   change "those" to --these--.

Claim 3, line 2:   delete "carrier" and after "is" insert --supported on--.

Signed and Sealed this

Ninth Day of July, 1991

*Attest:*

HARRY F. MANBECK, JR.

*Attesting Officer*   *Commissioner of Patents and Trademarks*